(12) United States Patent
Francois

(10) Patent No.: US 9,724,271 B2
(45) Date of Patent: Aug. 8, 2017

(54) METHODS AND ARTICLES FOR PREVENTING OR REDUCING RISK OF DEVELOPING A HYPERALLERGENIC IMMUNE SYSTEM

(75) Inventor: Cedric Francois, Louisville, KY (US)

(73) Assignee: Allovate, LLC, New York, NY (US)

( * ) Notice: Subject to any disclaimer, the term of this patent is extended or adjusted under 35 U.S.C. 154(b) by 658 days.

(21) Appl. No.: 13/695,182

(22) PCT Filed: May 2, 2011

(86) PCT No.: PCT/US2011/034741
§ 371 (c)(1),
(2), (4) Date: Nov. 21, 2012

(87) PCT Pub. No.: WO2011/137422
PCT Pub. Date: Nov. 3, 2011

(65) Prior Publication Data
US 2013/0218132 A1      Aug. 22, 2013

Related U.S. Application Data

(60) Provisional application No. 61/329,726, filed on Apr. 30, 2010.

(51) Int. Cl.
| | |
|---|---|
| *A61K 39/00* | (2006.01) |
| *A61K 39/35* | (2006.01) |
| *A61K 39/36* | (2006.01) |
| *A61K 39/38* | (2006.01) |
| *A61J 7/00* | (2006.01) |

(52) U.S. Cl.
CPC ............ *A61J 7/0053* (2013.01); *A61K 39/36* (2013.01)

(58) Field of Classification Search
None
See application file for complete search history.

(56) References Cited

U.S. PATENT DOCUMENTS

| | | | |
|---|---|---|---|
| 6,042,812 A | 3/2000 | Sanker et al. | |
| 6,113,887 A | 9/2000 | Mori et al. | |
| 6,821,507 B2 | 11/2004 | Glandorf et al. | |
| 7,300,645 B2 | 11/2007 | Takatsuka et al. | |
| 2004/0166123 A1* | 8/2004 | Jacobi et al. | 424/275.1 |
| 2004/0258896 A1* | 12/2004 | Yang | A61K 9/006 428/220 |
| 2005/0197319 A1 | 9/2005 | Nonomura et al. | |
| 2006/0058845 A1* | 3/2006 | Fuisz | A61J 7/0046 606/234 |
| 2006/0171968 A1* | 8/2006 | Brimnes | A61K 39/35 424/275.1 |
| 2007/0110673 A1 | 5/2007 | Spertini et al. | |

FOREIGN PATENT DOCUMENTS

| | | |
|---|---|---|
| EP | 0416816 A1 | 3/1991 |
| JP | 09-059179 | 3/1997 |
| WO | 93/01213 | 1/1993 |
| WO | 2005000199 A2 | 1/2005 |
| WO | 2006050729 A2 | 5/2006 |
| WO | 2006072251 A1 | 7/2006 |
| WO | 2007081948 A2 | 7/2007 |
| WO | 2007084587 A2 | 7/2007 |
| WO | 2008/098749 A2 | 8/2008 |
| WO | 2008100434 A1 | 8/2008 |
| WO | 2008/156704 A2 | 12/2008 |
| WO | 2010/128364 A1 | 11/2010 |

OTHER PUBLICATIONS

Mukherjee et al. 'Allergic Asthma: Influence of Genetic and Environmental Factors.' J. Biol. Chem. 286(38):32883-32889, 2011.*
Kurucz etal. 'Current Animal Models of Bronchial Asthma.' Curr. Pharm. Des. 12:3175-3194, 2006.*
Asturias J.A. et al., Tolerance and immunological changes of chemically modified allergen vaccine of Parietaria judaica in accelerated schedules, Clinical and Experimental Immunology, Dec. 5, 2006, 147:491-496, 147, British Society for Immunology.
Calderon M., et al., Specific Immunotherapy with High Dose SQ Standardized Grass Allergen Tablets was Safe and Well Tolerated, J. Investig Allergol Clin Immunol, 2006, 16(6) 338-344.
Didier A., et al., Optimal dose, efficacy, and safety of once-daily sublingual immunotherapy with a 5-grass pollen tablet for seasonal allergic rhinitis, American Academy of Allergy, Asthma & Immunology, 2007, pp. 1338-1345; DOI:10.1016/j.jaci.2007.07.046.
Frati F., et al., Development of a sublingual allergy vaccine for grass pollinosis, Drug Design, Development and Therapy, 2010(4), pp. 99-105.
Futamura N., et al., Characterization of genes for novel thaumatin-like proteins in Cryptomeria japonica, Tree Physiology, Oct. 3, 2005; (26)51-62; Heron Publishing, Victoria, Canada.
Futamura N., et al., Isolation and Characterization of cDNAs that Encode Homologs of a Pathogenesis-related Protein Allergen from Cryptomeria japonica, Biosci. Biotechnol. Biochem., 66 (11), 2495-2500, 2002.
Committee for Medicinal Products for Human Use (CHMP), Guideline on the Clinical Development of Products for Specific Immunotherapy for the Treatment of Allergic Diseases, European Medicines Agency, Nov. 20, 2008, pp. 1-13; London, UK.
Ivanciuc O., et al., SDAP: database and computational tools for allergenic proteins, Nucleic Acids Research, 2003, vol. 31, No. 1, pp. 359-362; DOI: 10.1093/nar/gkg010.
Kamdar T., et al., Immunotherapy in food allergy, Immunotherapy, May 1, 2010; 2(3):329-338; DOI:10.2217/imt.10.15.
Kleine-Tebbe J., et al., Safety of a SQ-standardised grass allergen tablet for sublingual immunotherapy: a randomized, placebo-controlled trial, Allergy, 2006, 61:181-184; Blackwell Munksgaard; DOI: 10.1111/j.1398-9995.2006.00959.x.
Lindbo, J., High-efficiency protein expression in plants from agroinfection-compatible Tobacco mosaic virus expression vectors, BMC Biotechnology, 2007(7):52; DOI:10.1186/1472-6750-7-52; http://www.biomedcentral.com/1472-6750/7/52.

(Continued)

*Primary Examiner* — Nora Rooney
(74) *Attorney, Agent, or Firm* — Dinsmore & Shohl LLP

(57) ABSTRACT

Infant pacifiers, compositions, and methods of use thereof, for preventing or reducing risk of developing a hyperallergenic immune system or allergic condition are provided.

17 Claims, No Drawings

(56) References Cited

OTHER PUBLICATIONS

Lizaso M.T., et al., Biological standardization and maximum tolerated dose estimation of an Alternaria alternata allergenic extract, J. Investig Allergol Clin Immunol 2006; vol. 16(2): 94-103.

Matsumura D. et al., Detection of New Antigenic Proteins in Japanese Cedar Pollen, Biol. Pharm. Bull 2006; 29(6) 1162-1166, Pharmaceutical Society of Japan.

Namba M., et al., Molecular cloning of the second major allergen, Cry j II, from Japanese cedar pollen, Federation of European Biochemical Societies (FEBS), FEBS Letters 353 (1994): 124-128.

Okubo K., et al., Allergen Immunotherapy for Allergic Rhinitis, J Nippon Med Sch. 2010: 77(6)285-289.

Okubo K., et al., Sublingual Immunotherapy for Japanese Cedar Pollinosis, Allergology International, 2009;58 (2):149-154; DOI: 10.2332/allergolint.08-RAI-0072.

Tong JC, et al., Allergen Atlas: a comprehensive knowledge center and analysis resource for allergen information, Bioinformatics, 2009, vol. 25(7): 979-980; DOI: 10.1093/bioinformatics/btp077.

Tsunematsu M., et al., Effect of Cry-consensus Peptide, a Novel Recombinant Peptide for Immunotherapy of Japanese Cedar Pollinosis, on an Experimental Allergic Rhinitis Model in B10.S Mice, Allergology International, 2007, 56(4):465-472; DOI: 10.2332/allergolint.O-07-495.

Yokozeki H., et al., Japanese Cedar Pollen as an Exacerbation Factor in Atopic Dermatitis: Results of Atopy Patch Testing and Histological Examination, Acta Derm Venereol, 2006; 86: 148-151; DOI: 10.2340/00015555-0020.

J.P. Allam et al, "Distribution of Langerhan cells and mast cells within the oral mucosa: new application sites of allergens in sublingual immunotherapy?", Allergy 2008: 63: 720-727.

English Abstract of JP 09-059179.

Notification of Reexamination (Office Action) from corresponding Chinese Application No. 201180032178.9 dated Sep. 30, 2016.

\* cited by examiner

METHODS AND ARTICLES FOR PREVENTING OR REDUCING RISK OF DEVELOPING A HYPERALLERGENIC IMMUNE SYSTEM

The present application claims priority under 35 U.S.C. §119(e) to U.S. Provisional Application Ser. No. 61/329,726 filed Apr. 30, 2010.

The invention relates to an oral mucosa-targeted immunotherapy of infants from birth to about age three months to prevent development of a hyperallergenic immune system wherein the immunotherapy is effectuated by delivery of allergens via a pacifier.

Demographic studies confirm the observation among clinicians that incidence of allergy and comorbid disorders is spiking dramatically, in particular in Western cultures. Allergy is considered an acquired disorder of the immune system. In affected individuals, ordinarily harmless environmental allergens trigger the allergic response characterized by excessive activation of mast cells and basophils by IgE, resulting in an extreme inflammatory response. Life-threatening anaphylactic reactions may occur in response to very specific allergens. Allergic hypersensitivity is known to develop very early in life and the general scientific consensus is that certain infants are born predisposed to developing an allergic immune system profile.

Most human infants are born with a Th2-biased immune response which is an artifact of the gestational period. Sometime between birth and about three months of age the Th1/Th2 balance matures and the immune system switches to provide a substantially Th1 biased immune response. In some infants, however, the switch fails and the immune system develops an abnormal response profile to environmental allergens. These children are prone to developing "atopic syndrome," a syndrome which includes the hyperallergenic disorder triad of atopic eczema, atopic rhinitis and asthma. People exhibiting the precipitating immune profile are said to possess an "atopic constitution." The general consensus among scientists and medical practitioners is that the atopic constitution has a very strong genetic component, but that environment is a large variable component to degree of expression.

The hygiene hypothesis has been proposed as a paradigm for explaining the recent spike in prevalence of atopic syndrome. According to this paradigm, an overly sterile environment during the critical Th switching phase disrupts maturation of the immune system leaving the infant with a substantially imbalanced immune response that results in hypersensitivity to allergens, over production of IgE and clinical symptoms of allergy.

The art of allergen-based immunotherapy (AIT) has been practiced for more than a century, beginning generally with the development in 1903 by William Dunbar of a conceptual immunization for hay fever using grass pollen, with the first successful such immunization reported in 1914. AIT consists in the gradual administration of increasing doses of a specific allergen in order to decrease the clinical reactivity to the allergen in a sensitized subject. By 1919 subcutaneous injection treatment (SCIT) for allergic desensitization was widely practiced for many different allergens and perennial treatment became the norm. A more recently developed version of AIT is sublingual immunotherapy (SLIT), wherein allergens are delivered through the buccal mucosa under the tongue. SLIT was first introduced as part of a maintenance protocol following SCIT therapy. As allergen extract technology and delivery method technologies evolved, the efficacy of SLIT increased. Due to its relatively cheap and convenient administration, which does not require either a clinical setting or technician, SLIT has become a focus for the development of new therapies, in particular for pediatric populations.

The efficacy of SLIT in preventative immunotherapy in children has been validated by several large studies, including the well-known PAT-trial. In 2002, Moller et al published the results of a large multicenter trial involving 205 children ages 6-14 years with grass and/or birch pollen allergy, in the absence of other allergies, and all subjects reported moderate to severe hay fever symptoms. The trial was designed to study the efficacy of SLIT in a preventative context with respect to asthma ("Pollen immunotherapy reduces the development of asthma in children with seasonal rhinoconjunctivitis; the PAT-Study, J Allergy Clinical Immunol. 2002; 109:251-6). The children were randomized either to receive specific immunotherapy for three years or to an open controlled group. At the onset of the study 20% of the children had mild asthma symptoms during the pollen season though none of the children had clinical asthma that required treatment on a daily basis. Methacholine bronchial provocation tests were carried out during the pollen season and across the winter. At the end of the three year trial, out of 150 children who had no asthma at the trial's onset, 24% of the SLIT group and 48% of the control group developed asthma using clinical standards.

Fanta et al. (Int. Arch. Allergy Immunol, 1999, 120: 218-224) reports a study of the immunological changes induced by SLIT in group of grass pollen allergic patients selected according to the criteria of having clinical symptoms including rhinitis and/or seasonal bronchial asthma during the grass pollen season, a positive skin prick test to grass pollen extracts, and specific IgE to grass pollen as determined by RAST-CAP. The SLIT was carried out by sublingual administration of drops of allergen extract.

WO 95/17208 discloses a method of prevention of allergic disease comprising administering to a previously unsensitised subject a dose of an allergen effective to induce establishment of a stable population of allergen-specific T-helper-1-like memory lymphocytes capable of inhibiting activity of allergen-specific-specific T-helper-2-like lymphocytes. The subject to be treated is preferably between 3 months and 7 years. House dust mites, grass pollen and tree pollen are mentioned as allergens and administration was carried out by the oral, intranasal, oronasal, rectal, intradermal, intramuscular or subcutaneous route.

While these results are impressive, they still represent a failure of therapeutic efficacy in a large number of children, and there was very little difference in the outcomes for children who exhibited asthmatic symptoms at the onset of therapy. The general theory behind projected efficacy of SLIT is the presence of dendritic cells, a form of allergen presenting cell considered critical to immune response, in the oral mucosa. Humans appear to be programmed to develop oral tolerance to environmental antigens rapidly and efficiently and SLIT is thought to exploit these mechanisms to promote a more tolerant systemic response. Hence, for pediatric populations SLIT has become a treatment of choice.

Generally, where sublingual and/or buccal delivery is desired in very young infants, delivery is by placement of droplets directly on the mucosa. These method suffer from the deficiency that in very young infants exposure is for a relatively brief period of time and repeated applications may be necessary to achieve a level of exposure that functionally mimics environmental exposure to target allergens that would occur in a natural environment. Repeated applications in droplet form into the oral cavity is likely to end up with substantial allergenic active entering the digestive system. Use of solid dissolving forms including, for example, lozenges, gel caplets and gel strips is clearly foreclosed in infants as presenting a potential choking hazard.

The preventative immunotherapy art to date fails to provide therapies and delivery mechanisms suitable for very young infants during the critical age range implicating Th switching and immune system priming. There remains a need in the art for convenient and effective methods for delivering immune-system priming allergens to children during the developmentally critical age of between newborn and about 3 months of age in order to achieve a more robust preventative effect.

Accordingly, the present inventors discovered that allergenic formulations may be safely, effectively and conveniently delivered to very young infants via an infant pacifier. Many suitable infant pacifiers specially adapted for delivery of medicinal compositions to infants can be used in embodiments of the invention. Generally, dosage forms include an organic or aqueous based liquid, gel or matrix (e.g., starch filler matrix) impregnated with or otherwise binding or physically associated with one or more allergenic agents. Delivery rate may be controlled by nipple member pore size, viscosity of the formulation or binding characteristics of the filler matrix.

According to one embodiment of the invention, an infant's pacifier is provided for containment and delivery of a composition, e.g., a pharmaceutical composition, formulated to prevent or reduce the risk of developing a hyperallergenic immune system disorder. The pacifier comprises a porous synthetic nipple removably attached to a base member, wherein the pacifier is adapted to receive a dosage form of the pharmaceutical composition. The containment area for containment of the formulation may be located in either the nipple member or the base member.

Another embodiment is directed to methods for preventing or reducing a risk of developing a hyperallergenic immune system disorder in a human. The method comprises exposing the oral mucosa of a human infant to at least daily sustained contact with one or more allergens, wherein the human infant is between the ages of birth and about six months when daily sustained contact is initiated, and daily sustained contact continues thereafter for at least about three months. In specific embodiments, daily sustained contact is initiated before the age of three months, and in very specific embodiments the daily sustained contact begins at birth. Daily sustained contact is achieved by suckling of the infant on a pacifier comprising an allergenic formulation.

Methods for restoring a Th1/Th2 balance in a human infant are also provided. The methods promote induction of a Th1-biased immune response during a developmentally critical period and comprises exposing the oral mucosa of a human infant to at least daily sustained contact with one or more allergens for a period of at least about three months, wherein daily sustained contact is initiated when the infant is between the ages of birth and about six months, wherein the daily contact is achieved by providing the infant with a pacifier comprising an allergenic formulation according to the invention. In specific embodiments daily sustained contact is initiated within one month of birth.

All references (e.g., printed publications such as books, papers, patents, patent applications, catalogs, databases) are incorporated herein by reference. In the event of a conflict or inconsistency, the present specification, as modified by any amendments thereto, shall control.

There has been a tremendous world-wide increase in the incidence of asthma and allergic rhinitis over the last two decades. Further, the increased rate of allergic rhinitis is thought to underpin the startling increase in development of comorbid airway diseases primarily among children in Western cultures, including otitis media, sinusitis, sleep apnea, upper respiratory infections, nasal polyps, hearing and speech disorders, and asthma.

From a very early age certain people appear particularly vulnerable to developing a hyperallergenic immune system and these people are generally referred to as possessing an "atopic constitution." Children who exhibit atopic syndrome typically develop symptoms including eczema, hayfever and asthma, which have come to be known as the "allergic triad." Atopic children also have an unusually high incidence of food allergies, and other symptoms characterized by their hyperallergic state. Unfortunately, children with atopic syndrome are at risk of dying from serious anaphylactic allergic reactions brought about by exposure to certain food or environmental allergens. Generally, atopy may be clinically defined by the presence of elevated levels of total and allergen-specific IgE in serum reflected by positive skin-prick tests to common allergens.

Infants contemplated as particularly benefited by the instant invention express a phenotype that is often referred to in the art as atopic syndrome. Such infants are very prone to developing hyperallergenic responses and researchers have discovered that most childhood asthmatics have atopic syndrome. There appears to be a strong genetic factor and a hyperallergenic response begins to develop very early in life with clinical symptoms of atopic eczema or dermatitis, allergic rhinitis, and asthma manifesting before the age of one.

The "hygiene hypothesis" is a popularly accepted paradigm that seeks to explain to rise in atopic syndrome and disease in Western society. Aside from genetic factors, it is clear that environment plays some role in expression. The hygiene hypothesis posits that excess cleanliness/sterility of the environment has led to a decline in the number of infectious stimuli so that insufficient quantities are present for proper development of the human immune system.

The modern theory of allergy is that it reflects a Th2 weighted imbalance, and immunologists have focused on methods for redirecting an inflated allergic Th2 response in favor of Th1 responses in an effort to reduce the incidence of atopy. In two broad approaches, researchers use high dose exposure to allergen to drive up the Th1 response in established diseases, while others focus on development of mycobacterial vaccines intended to drive a stronger Th1 response in early life. A specific immune response, such as the production of antibodies against a particular pathogen, is known as an adaptive immune response. This response can be distinguished from the innate immune response, which is an unspecific reaction towards pathogens. Allergy vaccines and Allergy immunotherapy in general address the adaptive immune response, which includes cells and molecules with antigen specificity, such as T-cells and the antibody producing B-cells. B-cells cannot mature into antibody producing cells without help from T-cells of the corresponding specificity. T-cells that participate in the stimulation of allergic immune responses are primarily of the Th2 type.

Establishment of a new balance between Th1 and Th2 cells has been proposed to be beneficial and central to the immunological mechanism of specific allergy vaccination. Whether this is brought about by a reduction in Th2 cells, a shift from Th2 to Th1 cells, or an up-regulation of Th1 cells is still controversial, however it is apparent that developmental AIT restores an appropriate Th1/Th2 balance.

T lymphocytes expressing CD4 are also known as helper T cells (Th), and these are regarded as being the most prolific cytokine producers. This subset can be further subdivided into Th1 and Th2, and the cytokines they produce are known as Th1-type cytokines and Th2-type cytokines. Cytokines are responsible for the clinical manifestations of the disease. Th1-type cytokines tend to produce the proinflammatory responses responsible for killing intracellular parasites and for perpetuating autoimmune responses. Interferon gamma is the main Th1 cytokine. Excessive proinflammatory responses can lead to uncontrolled tissue damage, so there needs to be a mechanism to counteract this. The Th2-type cytokines include interleukins 4, 5, and 13, which are associated with the promotion of IgE and eosinophilic responses in atopy, and also interleukin-10, which has more of an anti-inflammatory response. In excess, Th2 responses will counteract the Th1 mediated microbiocidal action. The optimal scenario would therefore seem to be that humans should produce a well balanced Th1 and Th2 response, suited to an immune challenge.

Recent strategies focus on prevention of the onset of hypersensitization, in particular in vulnerable children of atopic parents. In studies of pregnancy and early postnatal life, it has been found that a strong Th2 bias exists, which is thought to reduce the risk of miscarriage and to provide the relatively strong Th2 response necessary to modify Th1 cellular response in utero. Early in pregnancy, the fetus is capable of initiating an immune response. Since pregnancy is a Th2 state, babies tend to be born with Th2 biased immune responses. Very early microbiological exposure and early exposure to allergens can rapidly switch off the Th2 response and transition the bias. Researchers have also discovered subsets of infants who progress to development of allergic disorders who are born with a generally weaker Th1 response, or who are born having weak Th1 and Th2 responses.

Immunotherapies targeted to oral, nasal, vaginal, sublingual, ocular, rectal, urinal, pulmonal, otolar and buccal are all known in the art. The mouth, however, provides a major intake orafice for potential allergens. Humans are wired to develop "oral tolerance," and high concentration of dendritic cells are believed to play a role in this enhanced development of oral tolerance. Dendritic cells capture allergen, transport it to T-cells triggering a decrease in IgE antibody response and priming of mast cells.

Oral tolerance is considered one of the most critical forms of acquired tolerance and probably evolved to prevent hypersensitivity reactions to food proteins and bacterial antigens present in the mucosal flora. The oral mucosa is believed to specialized for enhanced maturation of immunity since it is in nearly constant communication with the environment from birth, either by inhalation or intake of food and liquid, and is in constant immunological communication with the bacterial antigens of the mucosal flora. The presence of dendritic cells in the oral mucosa is thought to be a large factor in the development of oral tolerance. Buccal and sublingual administration is less invasive, cheaper and more convenient than subcutaneous injection, and compliance with recommended treatment protocols is substantially greater.

Treatment methods focusing on buccal and sublingual routes of administration are becoming more widely accepted as efficacious. The oral mucosa is known to possess dendritic cells. A dendritic cell belongs to a class of cells known as antigen-presenting cells (APC). These cells display both foreign antigen complex and major histocompatibility complex on the surface, which T-cells recognize. The APCs process antigens and present them to T cells which results in activation of the T-cell. Although there are several types of APCs, dendritic cells have the broadest range of antigen presentation and are widely considered the most important APC. In particular, activated dendritic cells are extremely potent Th cell activators. Generally a dendritic cell may be considered a messenger between innate and adaptive immunity. Dendritic cells are found in some quantity in cells that communicate with the external environment, in particular in the skin, which comprises a specialized dendritic cell known as Langerhans cells. Once activated, a DC migrates to the lymphoid tissue to interact with T-cells and B-cells.

Skin and mucosal-associated lymphoid tissue-based DCs recognize pathogens which enter these areas and once the pathogenic material is processed the DC exits through afferent lymphatics to the lymphoid organs. During the migration the DC matures, characterized by expression of HLA on the surface. HLAs mediate presentation to the T-cells.

In certain embodiments of the invention, infants are exposed to allergens during the critical phase for transition of the immune response to a Th1 based response.

Hence, one embodiment of the invention provides methods for restoring a T1/T2 balance in a human infant by promoting induction of a Th1-biased immune response during the developmentally critical period. By use of a pacifier adapted to contain an allergenic composition, the natural suckling activity of the infant results in delivery of the composition through the nipple member of the pacifier resulting in entry of the composition comprising allergens into the oral cavity and dispersion over the oral mucosa. The nipple member of the pacifier may be porous or it may comprise as few as one hole for delivery. In this manner the oral mucosa of the human infant may be exposed to sustained contact with the allergenic actives across the critical age of between birth and about three months until achievement of the switch. Daily use of the adapted pacifier is contemplated and the composition may comprise one or more allergens. In specific embodiments the contact is daily sustained contact and is initiated in the first three months of life and continues for at least about three months. In other specific embodiments daily sustained contact is initiated at birth, and in further specific embodiments daily sustained contact is initiated at birth and continues until about three to six months of age. In some embodiments use is initiated when an infant is less than about 24 hours old, between 24-72 hours old, between 3-7 days old, or between 7-14 days old. It is contemplated that a regimen of dosing as close to daily sustained contact as possible, termed herein as substantially daily sustained contact, is within the scope of the invention, given ordinary uncertainties in the daily lives of infants. Use of an inventive pacifier less frequently than daily, e.g., on alternate days or several times a week is contemplated in certain embodiments. Embodiments in which daily use is interrupted, e.g., for relatively brief periods such as one to several days to a week, are within the scope of the invention.

The art is replete with examples of pacifiers adapted in various ways for the delivery of medicinals. Specific, non-limiting examples which provide guidance for selection of pacifiers suitable for the instant invention include U.S. Pat. No. 4,078,566 "Unit-dosing nipple"; U.S. Pat. No. 5,078,734 "Medication disposing pacifier"; U.S. Pat. No. 5,512,047 "Medicine dispensing pacifier"; U.S. Pat. No. 5,514,142 "Dispensing pacifier"; U.S. Pat. No. 5,601,605 "Infant pacifier fluid administrating unit"; and U.S. Patent Application Serial No. US20090182308 "Method and devices to administer medicine as a pacifier". The disclosures of these patents are fully incorporated herein by this reference.

In aspects of the invention, an infant's pacifier is adapted specifically for containment and delivery of a composition, e.g., a pharmaceutical composition, formulated to prevent or reduce the risk of developing a hyperallergenic immune system disorder. In a specific embodiment, the pacifier comprises a porous synthetic nipple removably attached to a base member and the pacifier is adapted to receive a dosage form of the pharmaceutical composition. In certain specific embodiments a reservoir for containing the composition is located in the nipple member, while in other specific embodiments the reservoir is located in the basemember. Dosage forms comprising one or more allergens are provided by the present invention, wherein the dosage form is suitable for insertion into a pacifier.

Allergens according to the invention may include any agent which triggers a measurable immune response. For example, an allergen may include any agent which triggers measurable production of IgE in at least some individuals exposed to the allergen (e.g., at least some atopic individuals). In many embodiments, an allergen comprises an agent that triggers an allergic reaction (type I hypersensitivity reaction) in at least some individuals exposed to the allergen (e.g., at least some atopic individuals). In some embodiments of the invention, the allergen is an air-borne allergen. Typically, the main route by which subject are exposed to such allergens is though inhalation. In some embodiments of the invention, the allergen is one to which subjects are mainly exposed by skin contact with the allergen. In some embodiments of the invention, the allergen is one to which subjects are mainly exposed by ingesting the allergen. In some embodiments of the invention, the allergen is one to which subjects are mainly exposed by injection.

Exemplary allergens according to the invention include allergens of plant, animal or fungal origin. Plant allergens include pollen, sap, leaves and plant toxins, while examples of fungal allergens include polypeptides produced by molds, *Aspergillus* and others. Animal allergens include polypeptides produced by insects, fecal allergens of dust mites and mammals, in particular of cats, and animal keratinacious dander. Specific examples include ragweed pollen, dust mite and dust mite excrement, animal dander and mold. Researchers have discovered that a combination of ragweed pollen and dust mite provides close to a "universal allergen" capable of affording desensitization to a wide variety of allergens, and capable of substantially reducing the risk of developing atopic syndrome in subjects with an atopic constitution. Other examples of allergens include food allergens, various insect venoms, and a number of industrial chemicals and pharmaceutical agents (e.g., penicillins, cephalosporins, cancer chemotherapy drugs, etc). Common sources of food allergens include peanuts, tree nuts, eggs, milk, shellfish (e.g., shrimp, crab), fish, wheat, soy and their derivatives.

One of ordinary skill in the art will appreciate that, in general, particular allergenic molecules (e.g., particular proteins) within allergens such as pollens, dusts, danders, molds, foods, etc, are responsible for triggering the allergic reaction. It is common to refer both to the particular allergenic molecules (e.g., particular proteins) and the materials in which they are found as "allergens", and that convention is use herein. Thus, reference to an "allergen" encompasses allergens in natural forms such as pollens, dusts, danders, molds, foods, or venoms, extracts of such natural forms of allergens, and allergenic molecules (e.g., particular proteins) that are at least partially purified or substantially purified or isolated from natural sources or produced using, e.g., recombinant DNA technology. The terms "protein" and "polypeptide" are used interchangeably herein. It will be appreciated that proteins can have modifications such as glycosylation, phosphorylation, acetylation, etc., and that a protein may be a single amino acid chain or can comprise multiple chains.

An allergen may be a modified form of a naturally occurring allergen. For example, an allergen can be chemically modified, e.g., to reduce its allergenicity. Such modified allergens may be referred to as an "allergoid". Allergoids may, for example, comprise allergens that have been treated with glutaraldehyde, formaldehyde or carbamoylated. They may be polymerized or in monomeric form.

Many allergens contain multiple distinct allergenic proteins. Numerous specific allergenic proteins have been isolated from the natural allergen form in which they occur and/or cDNA encoding such protein(s) has been isolated and sequenced. Amino acid sequences of numerous protein allergens are available. Allergens may be designated as "major" and "minor" allergens. In some embodiments, a protein is considered a major allergen if the prevalence of IgE reactivity is >50% among individuals sensitive to the natural form of an allergen in which the protein occurs, with other allergens being considered "minor" allergens. In some embodiments, an allergen is a protein for which the prevalence of IgE reactivity is >5% among individuals sensitive to the natural form of an allergen in which the protein occurs. Protein allergens of animal, plant, or fungal origin are usually named using a systematic nomenclature developed by the World Health Organization and International Union of Immunological Societies (WHO/IUIS) Allergen Nomenclature Sub-committee under the auspices of the WHO and IUIS (see, e.g., Lockey, R F and Ledford, D K (eds.) "Allergens and Allergen Immunotherapy" 4th ed. 2008. Informa Healthcare, New York, incorporated by reference herein, e.g., Chapman M D. Allergen Nomenclature. Chapter 3 (pp. 47-58) therein. According to this nomenclature, the first three letters of the genus are followed by the first letter of the species and then a numeral. For example: Phl p 5 is a major allergen of *Phleum pretense* (timothy grass) pollen. The WHO/IUIS Allergen Nomenclature Sub-committee maintains an allergen database (WHO/IUIS Allergen Database) that contains numerous approved and officially recognized allergens. The database, which can be accessed on the website available at http://www.allergen.org, is searchable by allergen name and allergen source (common or scientific name). According to the WHO/IUIS nomenclature, isoallergens are defined as allergens from a single species, sharing similar molecular size, identical biological function, and greater than 67% amino acid sequence identity (Chapman M D, supra). It will be appreciated that multiple isoforms (variants that differ in amino acid sequence) of many allergens are found in nature. Isoallergens and isoforms are denoted by the addition of four numeral suffixes to the allergen name. The first two numerals distinguish between isoallergens and the last two between isoforms. Such two or four numeral suffixes will generally be omitted herein, but it should be understood that the various allergen isoallergens and isoforms known in the art are included within the scope of allergens of use in embodiments of the various aspects of the instant invention.

One of ordinary skill in the art will readily be able to obtain amino acid sequences for numerous protein allergens of plant, animal, or fungal origin, among others, as well as sequence of nucleic acids encoding such allergens, using publicly available information. For example, the WHO/IUIS Allergen Database provides UniProt accession number for numerous protein allergens and Genbank accession number for nucleic acids encoding them. SDAP (Structural Database of Allergenic Proteins) is a Web server (available at the University of Texas Medical Branch website available at http://fermi.utmb.edu/SDAP) that, among other things, allows the user to retrieve information for allergens (e.g., sequence information) from the most common protein sequence and structure databases (SwissProt, PIR, NCBI, PDB). The US National Center for Biotechnology Information (NCBI) databases (available at http://www.ncbi.nlm.nih.gov) such as GenBank provide information regarding amino acid sequences of numerous protein allergens and nucleic acids that encode them. UniProt accession numbers (acc. no.) for various allergens of interest are provided herein for illustrative purposes. The afore-mentioned databases are incorporated herein by reference, e.g., allergen names, accession numbers, and sequences, are incorporated herein by reference. One of ordinary skill in the art can readily identify sequences of other allergens. As noted above, one of ordinary skill in the art will appreciate that isoallergens and isoforms of many of these allergens exist. One of skill in the art will further appreciate that variations in one or more nucleotides of the nucleic acids encoding a particular protein may exist among individuals of a given species due to natural allelic variation. As a result of the degeneracy of the genetic code, many of these variations do not result in changes in amino acid sequence. One of ordinary skill in the art will further appreciate that an allergen protein may be synthesized as a precursor protein that contains one or more portions not found in the mature form. A mature allergen protein may have been processed intracellularly or extracellularly so as to remove one or more portion(s) of the preprotein. For example, a signal peptide may be removed, or a polypeptide chain may be cleaved to form two or more chains, optionally removing a portion of the precursor protein.

Plant pollens are major sources of airborne allergy throughout many areas of the world. In some embodiments of the invention, an allergen comprises grass pollen. Grasses, as used herein, include members of the family Poaceae (sometimes termed "true grasses"), rushes (Juncaceae) and sedges (Cyperaceae). Grasses are distributed widely throughout many regions of the world, with different species having variable importance in different geographical areas. For example, grass species common in at least some regions of Europe and/or the US include *Dactylis glomerata* (orchard grass), *Poa pratensis* (Kentucky bluegrass), *Lolium perenne* (ryegrass), *Anthoxantum odoratum* (sweet vernal), *Phleum pratense* (timothy), *Festuca eliator* (meadow fescue), *Agrostis alba* (redtop), and *Cynodon dactylon* (Bermuda grass). Grass allergens include, e.g., Poa a 1 (UniProt acc. no. Q9ZP03) and Poa p 5 (UniProt acc. no. Q9FPR0). In some embodiments of the invention, an allergen is from a grass within the *Dactylis, Poa, Lolium, Anthoxantum, Phleum, Festuca, Agrostis,* or *Cynodon* genus, e.g., any of the afore-mentioned species. For example, an allergen can comprise a Poa a, Poa p, or Phl p protein.

In some embodiments of the invention, an allergen is pollen (or an extract or component thereof) of a tree or shrub that is a member of the Cupressaceae family. It should be noted that the Cupressaceae (cypress) family includes a number of species whose common name includes the word "cedar". In some embodiments, the allergen is pollen from a species in the subfamily Cupressoideae, e.g., a member of the genus *Chamaecyparis* or *Juniperus* ("juniper"). In some embodiments, the allergen is pollen from *Cryptomeria japonica* (family Cupressaceae, subfamily Taxodioidea), commonly referred to as Sugi or Japanese cedar. Japanese cedar pollen is the major cause of pollinosis in Japan. Approximately 15% of the Japanese population was affected by Japanese cedar pollinosis in 2002 (Okuda M., Ann Allergy Asthma Immunol, 91: 288-96, 2003), and the prevalence has reportedly increased to an estimated 26.5% in 2008 (see Okubo, K., Allergol Int., 57(3):265-75 2008, incorporated by reference). Many patients with cedar pollinosis have also been sensitized to *Chamaecyparis obtusa* pollen (Japanese cypress, hinoki cypress or hinoki), which disperses after Japanese cedar pollen. In these individuals, symptoms of Japanese cedar pollinosis are frequently followed by those of cypress pollinosis, often resulting in a symptomatic period lasting for about 4 months (e.g., from February to May). In some embodiments, the invention provides compositions and methods of use in desensitizing individuals who suffer from Japanese cedar and/or Japanese cypress pollinosis. Cry j 1 (UniProt acc. no. P18632) and Cry j 2 (UniProt acc. no. P43212) are major allergens of *Cryptomeria japonica* pollen. See, e.g., Yasueda H, et al., J Allergy Clin Immunol., 71(1 Pt 1):77-86, 1983; Sakaguchi M, et al. Allergy, 45:309-312, 1990, for discussion. cDNAs encoding these allergen proteins have been cloned and sequenced. See, e.g., Sone T, et al., Biochem Biophys Res Commun. 199:619-625, 1994; Komiyama N, et al. Biochem Biophys Res Commun. 201:1021-1028, 1994; Namba M, et al., FEBS Lett. 353:124-128, 1994; and PCT/US1992/005661 (WO1993001213—ALLERGENIC PROTEINS AND PEPTIDES FROM JAPANESE CEDAR POLLEN). Cry j 3 has been identified, and sequences are available (see, e.g., Futamura N, et al. Biosci Biotechnol Biochem. 66(11): 2495-500, 2002; Futamura N, et al. Tree Physiol. 26:51-62, 2006). Other allergens, e.g., Cry j 4, Cry j 5, Cry j 6 have been identified as well (Matsumura D, et al., Biol Pharm Bull. 29(6):1162-6; 2006). In some embodiments, an allergen comprises a Cry j protein, e.g., Cry j 1, Cry j 2, Cry j 3, Cry j 4, Cry j 5, Cry j 6.

Cha o 1 (UniProt acc. no. Q96385) and Cha o 2 (UniProt acc. no. Q7M1E7) are major allergens of Japanese cypress, cDNAs for which have been cloned and sequenced (Suzuki M, et al., Mol Immunol. 33(4-5):451-60, 1996; Mori T, et al, Biochem Biophys Res Commun. 263(1):166-71, 1999). In some embodiments an allergen comprises a Cha o protein, e.g., Cha o 1, Cha o 2.

Ashe juniper (*Juniperus ashei*, family Cupressaceae, sometimes called mountain cedar) and Arizona cypress (*Cupressus arizonica*, family Cupressaceae) pollens cause seasonal allergic rhinitis in certain parts of the US and Northern Mexico while Italian cypresses (*Cupressus semperverins*, family Cupressaceae) cause pollinosis in the Mediterranean region (e.g., France, Italy, Israel). In some embodiments, the invention provides compositions and methods of use in desensitizing individuals who suffer from allergy to one or more such pollens. Jun a 1 and Jun a 2 are major allegens of juniper pollen. See, e.g., Midoro-Horiuti T, J Allergy Clin Immunol. 104(3 Pt 1):608-12, 1999; Midoro-Horiuti T, J Allergy Clin Immunol. 104(3 Pt 1):613-7, 1999; Yokoyama M, Biochem Biophys Res Commun. 275(1):195-202, 2000). The amino acid sequence of Jun a 1 (UniProt acc. no. P81294) shows significant identity with those of Cry j 1 and Cha o 1, respectively. The amino acid sequence of Jun a 2 (UniProt acc. no. Q9FY19) shows about 70% and 82% identity with those of Cry j 2 and Cha o 2, respectively. In some embodiments an allergen comprises a Jun a protein, e.g., Jun a 1, Jun a 2.

The Betulaceae, or birch family, includes six genera of deciduous nut-bearing trees and shrubs, including the birches (genus *Betula*), alders (genus *Alnus*), hazels (genus *Corylus*), hornbeams and hop-hornbeams. In some embodiments of the invention, the allergen comprises pollen (or an extract or component thereof) of a member of the birch family. In some embodiments the pollen is from a member of the subfamily Betuloideae. In some embodiments, the pollen is from genus *Betula*, e.g., *Betula verrucosa*. Birch pollen allergens include, e.g., Bet v 1, Bet v 2, Bet v 3, Bet v 4, Bet v 5, Bet v 6, and Bet v 7. In some embodiments, the pollen is from genus *Alnus*, e.g., *Alnus glutinosa*. Alder pollen allergens include, e.g., Aln g 1 and Aln g 4. In some embodiments, the pollen is from genus *Corylus*, e.g., *Corylus avellana*. In some embodiments, an allergen comprises a Bet v protein.

Various other plants that are significant causes of allergy belong to the families Asteraceae, Amaranthaceae, Urticaceae, Euphorbiaceae, and Plantaginaceae. In some embodiments of the invention, a composition comprises a pollen (or an extract or component thereof) from a plant of the Asteraceae, Amaranthaceae, Urticaceae, Euphorbiaceae, or Plantaginaceae family. Examples of such plants include ragweed, cocklebur, marsh elder, mugwort, feverfew, pellitory, goosefoot, plantain, and Russian thistle. Ragweeds (*Ambrosia* species), for example, are a genus of flowering plants from the sunflower family (Asteraceae) and represent a highly significant cause of allergy in North America that is becoming increasingly important in Europe. Four major families of proteins may represent the major cause of allergic reactions to pollens of such plants: the ragweed Amb a 1 family of pectate lyases (e.g., UniProt accession numbers P27759, P27760, P27761, P27762 from *Ambrosia artemisiifolia* (short ragweed)); the defensin-like Art v 1 family (e.g., from mugwort and feverfew, e.g., UniProt acc. no. Q84ZX5 from *Artemisia vulgaris* (mugwort)); the Ole e 1-like allergens, Pla l 1 from plantain, and Che a 1 from goosefoot, and the nonspecific lipid transfer proteins Par j 1 and Par j 2 from pellitory (Gadermaier G, et al. Curr Allergy Asthma Rep. 4(5):391-400, 2004)). Amb a 1 was among the first of these allergens for which cDNA was cloned and sequenced. See, e.g., PCT/US1990/001310 (WO/1990/011293—ALLERGENIC PROTEINS FROM RAGWEED AND USES THEREFOR). In some embodiments of the invention, an allergen comprises an Amb a, Art v, Ole e-like, Pla 1, Par j protein, or combination thereof. Mixtures of pollens from such plants (and extracts and components thereof) are contemplated. Plant allergens of natural rubber latex derived from a variety of different plant species (e.g., *Hevea*, such as *Hevea brasiliensis*) are contemplated.

Dust mites are significant sources of allergy in many areas of the world. Allergens are found in dust mite feces and the mite body. Dust mite species of significant importance include, for example, *Dermatophagoides farinae*, *D. pteronyssinus*, and *Tyrophagus putrescentiae*. House dust mite allergens include, for example, Der p 1 (UniProt acc. no. P08176), Der p 2 (UniProt acc. no. P49278), Der p 3 (UniProt acc. no. P39675), and Der p 4 from *D. pteronyssinus* and Der f 1 (UniProt acc. no. P16311), Der f 2 (UniProt acc. no. Q00855), and Der f 3 (UniProt acc. no. P49275) from *D. farinae*. In some embodiments of the invention an allergen comprises a Def p, Der f, or Tyr p protein.

Animal allergens occur, for example, in dander, feathers, hair, saliva, and excretions (e.g., urine). Domesticated animals such as cats (*Felis domesticus*) and dogs (*Canis lupus familiaris*) are common sources of allergy. Fel d 1 (UniProt acc. no. P30438 (chain 1); UniProt acc. no. P30440 (chain 2)), Fel d 3, and Fel d 4 are major cat allergens. Can f 1 (UniProt acc. no. O18873) and Can f 2 (UniProt acc. no. O18874) are major dog allergens. In some embodiments an allergen comprises a Can f or Fel d allergen. Rodents such as mice (e.g., *Mus musculus*), rats (e.g., *Rattus norvegicus*), and rabbits (e.g., European rabbit (*Oryctolagus cuniculus*)) are common sources of allergy. Identified allergens include, e.g., Mus m 1, Rat n 1, and Ory c 1, in these species, respectively. Individuals may, for example, encounter such animals as pets, as pests, or in an occupational context (e.g., as laboratory animals). In some embodiments an allergen comprises a Mus m, Rat n, or Ory c protein. Farm animals such as horses, cows, sheep, goats are also causes of allergy, and in some embodiments an allergen from such animal is present in an inventive composition.

Insects and insect venoms are notable sources of allergens. Cockroach allergens are significant causes of allergy in many areas of the world. Cockroach species include, for example, *Blattella germanica* (German cockroach) and *Periplaneta americana* (American cockroach), and *Blatta orientalis* (Oriental cockroach) Cockroach allergens include, for example, Bla g 1, Bla g 2, Bla g 5, Bla g 5, Bla g 6, Bla g 7, and Bla g 8 (from *B. germanica*) and Per a 1, Per a 3, Per a 6, Per a 7, Per a 9, and Per a 10 (from *P. Americana*). In some embodiments an allergen comprises a Bla g, Per a, or Bla o allergen. Ant, moths, fleas, flies (e.g., house fly, horse fly, mayfly), and mosquitos are also sources of allergens. In some embodiments an allergen is a cockroach, ant, moth, flea, fly, or mosquito protein.

Insect venoms, (e.g., from insects of the order Hymenoptera, e.g., bees, hornets, or wasps) that are potential causes of severe allergic reactions include venoms from European Hornet (*Vespa crabro*), Honey Bee (*Apis mellifera*), Hornet (*Dolichovespula* spp.), Paper Wasp (*Polistes* spp.), Yellow Jacket (*Vespula* spp.), White (Bald)-Faced Hornet (*Dolichovespula maculata*), Yellow Hornet (*Dolichovespula arenaria*). In some embodiments an allergen is a venom (or extract or component thereof) of a bee, wasp, or hornet. For example, an allergen can comprise an Api, Dol, or Ves protein.

Fungi (e.g., fungal spores or fragments (e.g., hyphal fragments)) are significant sources of allergy. *Alternaria* (e.g., *Alternaria alternata* (*Alternaria* rot fungus)), *Cladosporium* (e.g., *Cladosporium herbarum*, *Cladosporium cladosporioides*), *Aspergillus* (e.g., *Aspergillus fumigatus*, *Aspergillus niger*), *Fusarium, Penicillium* are exemplary allergenic fungi of interest. In some embodiments, an allergen comprises a protein found in or produced by *Alternaria, Cladosporium, Aspergillus, Fusarium, Penicillium*, or other fungus. For example, an allergen can comprise an Alt a, Asp a, Asp n, Cla or Pen protein.

Methods of obtaining allergens are well known in the art. For example, pollens can be collected from the respective plants, which may be cultivated or in the wild. Fungal extracts can be produced from pure culture mycelial mats or allergens can be isolated from culture medium. Rusts and smuts can be obtained from natural growths. Epithelial extracts can be produced from the hide, hair, or feathers containing the natural dander, or from separated dander. Insect and mite extracts can be produced from the whole body of the insects or mite, respectively. In the case of insect venoms, venom or venom-containing organs can be isolated or a whole body extract can be used. House dust can be made from various dusts ordinarily found in the home (e.g., upholstery dust, mattress dust, or general dust accumulating on surfaces). Other dusts (e.g., grain dust, wood dust, cotton dust) can be collected from the appropriate location. Food extracts can be prepared from the edible portions of the respective foods, e.g., freshly obtained foods.

Methods suitable for allergen processing, e.g., production of allergen extracts, purification of allergen molecules, etc., are well known in the art. Very briefly, source allergen material (e.g., pollen, insect, dander) can be subjected initially to pulverization, drying, defatting (by extraction using organic solvent), or other steps as appropriate for the particular allergen. Centrifugation can be used, e.g., to separate solid or particulate matter. Resulting material can be incubated in an aqueous medium (e.g., water or suitable buffered solution, e.g., ammonium bicarbonate, phosphate buffered saline, etc.) for a suitable period of time to at least partly solubilize proteins. Crude extract can be processed using, e.g., dialysis, filtration, fractionation, chromatography, etc. In some embodiments, one or more steps is performed to at least partly remove low molecular weight components, concentrate the extract, etc. Extracts can be sterilized, e.g., using filtration and/or irradiation. Other processing steps can be applied as known in the art. Numerous specific protocols are available.

Extracts of allergens specifically processed for use in human immunotherapy are available commercially. For example, GREER Laboratories Inc. Allergy and Immunotherapy division publishes the brochure Human Allergy Products and Services, available on-line at the company website currently at http://www.greerlabs.com/files/catalogs/HumanAllergyCatalog.pdf. GREER also publishes a brochure entitled "Source Materials Products and Services" available online at the company website currently at http://www.greerlabs.com/files/catalogs/SourceMaterialsCatalog.pdf, which details available allergens that can be used as raw materials for production of allergen extracts or more highly purified allergen protein preparations. Both publications are incorporated herein by reference. Other commercial suppliers of allergens and/or allergen extracts include ALK Abello, Inc., Allermed Labs, and HollisterStier. An extensive list of allergen extracts is found in Remington, supra. Allergen extracts typically contain multiple proteins, e.g., multiple allergenic proteins, present in the natural form of the allergen. Extracts can be prepared from, e.g., pollens (e.g., of trees, shrubs, grasses, other plants such as those often termed "weeds"), animal epithelia, feathers, fungal mycelia or spores, smuts, mites, insects, insect venoms, foods, dusts, etc. In some embodiments, an extract is prepared essentially from a single natural allergen (e.g., obtained from a single species of plant, animal, insect, fungus, etc.). Mixtures are contemplated. In some embodiments an extract is derived from multiple different plant pollens (e.g., weed mixture, tree mixture, grass mixture), multiple different fungi or smuts, multiple different insect venoms, multiple different animal epithelia, etc. Fungal extracts can be prepared from mycelia and/or spores (e.g., *Alternaria, Cladosporium*) and/or from culture filtrate material (e.g., *Aspergillus*). In some embodiments, one or more allergen protein(s) is further purified, e.g., from an extract comprising multiple proteins. One of ordinary skill in the art will readily be able to purify allergen protein(s) of interest using methods known in the art for protein purification. See, e.g., Cutler, P. (ed.) *Protein Purification Protocols, Methods in Molecular Biology*, Volume 244, 2004; Simpson, R J., et al., *Basic Methods in Protein Purification and Analysis: A Laboratory Manual* Cold Spring Harbor Laboratory Press, 2008; Richard R Burgess and Murray P. Deutscher (eds.) Methods in Enzymology: *Guide to Protein Purification*, $2^{nd}$ ed., Academic Press, 2009. Purification can entail chromatographic methods (e.g., based on size, hydrophobicity, affinity, etc.), immunological methods, electrophoretic methods, etc. Specific protocols for preparing various at least partially purified allergen proteins are available. In some embodiments, an extract or at least partially purified protein preparation comprises at least 70%, 80%, 90%, 95% or more protein by weight. In some embodiments, a protein is considered pure when it is removed from substantially all other compounds or entities other than a solvent and any ions contained in the solvent, e.g., the protein constitutes at least about 90%, e.g., at least 91%, 92%, 93%, 94%, 95%, 96%, 97%, 98%, 99%, or greater than 99% of the dry weight of the composition or on a weight per volume basis (excluding the solvent and ions). In some embodiments, a particular allergen protein of interest is considered pure if it constitutes at least about 90%, e.g., at least 91%, 92%, 93%, 94%, 95%, 96%, 97%, 98%, 99%, or greater than 99% of the protein content in the protein preparation by dry weight. Methods for assessing purity are known in the art and include, e.g., chromatographic methods, immunological methods, electrophoretic methods, mass spectrometry, etc. Any of the polypeptides described herein may be purified, in various embodiments. An extract or purified protein preparation can be provided in various formats. For example, an extract or purified protein preparation dried, e.g., lyophilized, or provided in aqueous medium, optionally comprising a protein stabilizing agent such as glycerin, a preservative, etc.

Mixtures of individual allergen proteins are contemplated. Allergen protein mixtures can comprise allergen proteins from the same species or from multiple different species, which may be in the same or different genera, subfamily, family, etc. In some embodiments, an allergen protein encoded by a gene homologous to that which encodes a particular allergen protein of interest can be used. For example, orthologous genes, i.e., genes in different species that are similar to each other because they originated by vertical descent from a single gene of the last common ancestor, can be used.

In some embodiments, an allergen comprises a recombinantly produced protein. Methods for producing proteins using recombinant DNA technology are well known in the art and are described in standard references such as Ausubel, F., et al., (eds.), *Current Protocols in Molecular Biology, Current Protocols in Immunology, Current Protocols in Protein Science, and Current Protocols in Cell Biology*, all John Wiley & Sons, N.Y., editions as of 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005, all of which are incorporated herein by reference. Any suitable vectors, e.g., plasmids, viruses (e.g., DNA or RNA viruses), cosmids, etc., can be used to introduce a nucleic acid that encodes an allergen protein into a host cell, in various embodiments. One of ordinary skill in the art would appreciate that due to the degeneracy of the genetic code, any of a wide variety of nucleic acid sequences can encode a protein of interest (e.g., an allergen) and can accordingly be used in various embodiments of the invention relating to recombinant production of allergens. In some embodiments, a nucleic acid sequence is codon optimized for production of the protein in a host cell of interest. Any suitable expression system can be used. Various host cells, e.g., bacterial, fungal, insect, vertebrate (e.g., mammal), can be used in various embodiments. In some embodiments a host cell is selected based at least in part on the allergen. For example, in some embodiments a plant allergen can be produced in plant cells; a vertebrate allergen can be produced in vertebrate cells; a fungal allergen can be produced in fungal cells. An allergen could be produced using a transgenic approach, e.g., a transgenic plant. In some embodiments, the sequence of a recombinantly produced allergen comprises a fragment or variant of the sequence of a naturally occurring allergen protein. For example, a fragment may be a continuous sequence consisting of at least 20%, 30%, 40%, 50%, 60%, 70%, 80%, 90%, or more of the full length naturally occurring allergen protein. A variant has one or more amino acid substitutions, deletions, or additions (e.g., insertions) as compared with a naturally occurring allergen protein. For example, a variant may comprise a sequence at least 70%, 80%, 90%, 95%, 96%, 97%, 98%, 99%, or more identical to a naturally occurring allergen protein over a window of at least 50%, 60%, 70%, 80%, 90%, 95%, 96%, 97%, 98%, 99%, or more of the naturally occurring antigen, allowing the introduction of gaps to maximize identity. Percent identity can be calculated with the use of a variety of computer programs known in the art. For example, computer programs such as BLAST2, BLASTN, BLASTP, Gapped BLAST, etc., generate alignments and provide percent identity between a sequence of interest and sequences in any of a variety of public databases. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs are used. A PAM250 or BLOSUM62 matrix may be used. See the Web site having URL www.ncbi.nlm.nih.gov for these programs. In a specific embodiment, percent identity is calculated using BLAST2 with default parameters. In some embodiments, a variant has up to about 1%, 5%, 10%, 20%, or 30% amino acid substitutions, insertions, or deletions. In some embodiments, a variant has between 1 and 10 amino acid substitutions, insertions, or deletions.

In some embodiments, an allergen may be a fusion protein comprising at least a portion of an allergen protein comprising at least one allergenic epitope and a heterologous polypeptide. In some embodiments, the fusion protein comprises a tag, e.g., an epitope tag, of use in purifying the protein. In some embodiments, an allergen, e.g., a fusion protein, is expressed in a plant, e.g., in leaves or seeds. Such leaves or seeds can be used to prepare a composition of this invention. For example, a nucleic acid encoding the allergen can be expressed under control of an appropriate promoter to achieve expression in the plant or a portion thereof. A plant can be a transgenic plant or the protein can be transiently expressed, e.g., using a viral vector. In some embodiments a fusion protein comprises an allergenic epitope (e.g., an epitope of Japanese cedar pollen or other allergenic pollen) fused with at least a portion of a seed storage protein such as glycinin. A fusion protein could comprise multiple different allergen proteins or portions thereof. Methods such as solid phase peptide synthesis or protein ligation could be used to synthesize polypeptides in some embodiments, particularly if relatively short.

In some embodiments, a polypeptide that comprises one or more epitope(s), e.g., epitope(s) recognized by human T-cells derived from a naturally occurring allergen is used as an allergen in the instant invention. In some embodiments, the polypeptide comprises human T-cell epitope(s) derived from at least two different allergens, e.g., 2, 3, 4, 5, 6, or more different allergens. In some embodiments, the total number of T-cell epitopes is between 2 and 10. The epitopes may be separated from each other by 1 or more amino acids that serve as a spacer. A spacer can be, e.g., 1, 2, 3, 4, or 5 amino acids long, up to about 25 amino acids. In general, any amino acids can be used as spacers. In some non-limiting embodiments, relatively small amino acids such as Gly, Ala, Ser are used, but other amino acids could be used. For example, Cry-consensus peptide is a polypeptide containing six major human T-cell epitopes derived from both Cry j 1 and Cry j 2 (Tsunematsu M, et al. Allergology International. 56(4):465-72, 2007). Its sequence is: MKVTVAFNQFGPN-RR-VFIKRVSNVIIHG-RR-IDIFASKNFHLQKNTIGTG-RR-WKNNRIWLQFAKLTGFTLMG-RR-LKMPMYIAGYKTFDG-RR-VDGIIAAYQNPASWK (SEQ ID NO: 1). The T-cell epitopes are underlined. Epitopes 1, 2, and 5 (starting from the left) are Cry j 1 epitopes. Epitopes 3, 4, and 6 are Cry j 2 epitopes. T cell epitopes of a variety of allergens have been identified and could be used in embodiments of the invention. An epitope can be a linear epitope or a conformational epitope.

In certain embodiments, the composition, e.g., pharmaceutical composition, comprises at least one allergen selected from the group of pollen, dust mite, mold and animal dander and the dosage form optionally comprises an extended release formulation of the composition, e.g., pharmaceutical composition. In very specific embodiments, the composition allergens consists of ragweed pollen and dust mite. In some embodiments, an allergen consists of a pollen allergen and an insect allergen. In some embodiments, an allergen consists of a pollen allergen and a mite allergen.

In some embodiments, an allergen extract is provided in a liquid form for inclusion in a composition of the invention. For example, an allergen extract can be provided in water, glycerin, or a combination thereof. In some embodiments, an allergen extract is provided in substantially dry form, e.g., as a powder, e.g., in lyophilized form. In some embodiments, an allergen-containing tablet such as those used in SLIT (or contents thereof) can be employed to produce a composition for use in a pacifier. The tablet can contain allergen extract in lyophilized form. In some embodiments, components of a five-grass pollen SLIT tablet (Stallergènes SA, France) can be used. The extracts are from pollen of perennial rye grass (*Lolium perenne*), meadow grass (*Poa pratensis*), timothy grass (*Phleum pratense*), cocksfoot (*Dactylis glomerata*) and sweet vernal grass (*Anthoxanthum odoratum*). and are sold under the name Oralair®. In some embodiments, components of a Grasax® tablet are used (ALK Grass tablet, ALK-Abelló A/S, Hørsholm, Denmark). The active substance in Grasax is a standardised allergen extract of grass pollen from timothy (*Phleum pratense*). Other ingredients in Grasax are gelatine (fish source), mannitol, and sodium hydroxide. Of course other excipients could be used or omitted as the case may be. Components can be mixed with a suitable fluid, e.g., a liquid, gel, etc., for inclusion in a pacifier of the invention.

One of ordinary skill in the art will appreciate that the amount of allergen(s) used in a composition of the invention can vary based on a number of factors such as, for example, the particular allergen(s) and the potency of the allergen preparation used. Allergens can be detected and/or quantified using methods known in the art, and such methods can be used to characterize allergen preparations (e.g., allergen extracts), e.g., with respect to allergen content and/or potency. For example, immunological methods such as immunoblotting or ELISA assays using, e.g., an appropriate monoclonal antibody, or other types of binding assays for detecting and/or quantifying proteins known in the art are applicable to many allergens of interest herein. Mass spectrometry could be used. In vivo or in vitro bioassays may be used to quantify biological activity. For example, skin prick tests can be performed on individuals known to be allergic to a particular allergen, and one or more indicators of allergic response (e.g., wheal area) or allergen-specific IgE production, can be measured. Skin prick tests can be standardized, e.g., using a specific delivery device, technique, and specified amount of allergen preparation. In vitro bioassays include measuring mediator release (e.g., histamine, cytokines, or lipid mediators) from appropriate cells, e.g., sensitized cells. An in-house reference standard can be produced (e.g., based on in vivo bioassays) and in vitro tests can be used to compare the potency of subsequent batches of allergen with the in-house reference and potency can be assigned as arbitrary units. A variety of units are in use to quantify allergen content and/or potency of allergen preparations. See, e.g., Remington, supra, and Lockey, R F and Ledford, D K, supra. For example, allergen content of allergen preparations can be expressed as weight-to-volume or Protein Nitrogen Units. In the US, standardized extracts are typically labeled as Allergy Units (AU)/ml or Bioequivalent Allergy Units (BAU)/ml. BAU is a standard established by the FDA, which provides a variety of different reference extracts that can be used to establish potency. In Japan, allergen content of allergen preparations is often expressed using Japanese Allergy Units (JAU) measured by ELISA. In Europe, a number of country-specific or company-specific standards are in use. For example, in-house reference standards can be established and used to quantify the strength of subsequently produced batches of allergen preparation. For example, an in-house reference index-of-reactivity (IR) can be used, wherein, for example, 100 IR/ml is defined as the concentration eliciting, by means of skin prick testing, a geometric mean wheal size of 7 mm in diameter in 30 patients sensitive to the corresponding allergen. If desired, any one or more of such approaches can be employed with regard to the allergen preparations of use in the instant invention.

In some embodiments, a composition of the invention can be formulated so that a typical daily or weekly usage provides between 1 pg to 15 mg of one or more allergen proteins(s), e.g., between ing and 1.5 mg of one or more allergen protein(s), e.g., between 100 ng and 100 μg of one or more allergen protein(s). In some embodiments, a composition of the invention can be formulated so that typical daily or weekly usage provides (e.g., on a daily basis or over a period of time such as a week) between 0.01 and 100 times an amount of allergen useful in a SLIT regimen, e.g., between 0.1 and 10 times, or between 0.5 and 2 times an amount useful in a SLIT regimen. For example, in some embodiments, a composition comprising Cry j 1 and/or Cry j 2 can provide between 20 JAU and 20,000 JAU on a daily or weekly basis, e.g., between 200 JAU and 2000 JAU. In some embodiments, a composition contains 1, 2, 3, 4, 5, or more allergen protein(s), wherein each allergen protein may independently be present in any of the afore-mentioned quantities and/or the total amount of allergen present may be any of the afore-mentioned quantities. One of skill in the art would readily select an effective amount for inclusion in a composition or product of the invention. Homeopathic amounts of allergen are also contemplated for use in inventive compositions. For example, a 30 c homeopathic dilution of an allergen extract or other allergen preparation can be used. As known in the art, a 30 c dilution represents 30 sequential 1 in 99 dilutions of the stock solution. In some embodiments, a 15 c to 60 c dilution is used. In some embodiments, the resulting solution theoretically contains no molecules of allergen or of the original solution.

In some embodiments of any aspect of the invention, an allergen can be associated with microparticles. For example, the allergen can be encapsulated by such particles and/or microparticles can be impregnated or coated or otherwise physically associated with allergen. "Microparticle" as used herein, encompasses any microscopic particles used to protect and/or deliver agents in areas such as pharmaceuticals, nutraceuticals, cosmeceuticals, cosmetics, food technology, and the like. Such particles may be referred to in the art as microcapsules, microspheres, nanospheres, nanoparticles, nanocapsules, liposomes, and the like. Methods of making and employing such delivery systems are well known in the art. Examples are described, e.g., in references such as: Lakkis, J M (ed.) Encapsulation and controlled release technologies in food systems (Wiley-Blackwell, 2007); Nedovic, V. and Zuuidam, N J (eds.) (Springer, 2009); Cohen, S. and Bernstein, H. Microparticulate systems for the delivery of proteins and vaccines (CRC Press, 1996); Jones, D., Pharmaceutical Applications of Polymers for Drug Delivery (ChemTec Publishing, 2004). Benita, S. (ed.) Microencapsulation: methods and industrial applications (Informa Healthcare; $2^{nd}$ ed., 2005). In some aspects, known approaches used in substances expected to contact the oral cavity (e.g., foods) are used in the present invention.

A number of polymeric delivery vehicles for providing sustained release are known in the art. One of ordinary skill would select appropriate polymers for use in various embodiments of the invention (e.g., in particle or matrix formulations). In some embodiments, a biocompatible polymer, which may be biodegradable, may be used. The polymers may be homopolymers, copolymers (including block copolymers), straight, branched-chain, or cross-linked. Natural or synthetic polymers can be used in various embodiments of the invention. Polymers include, but are not limited to, poly-lactic acid (PLA), poly-glycolic acid (PGA), poly-lactide-co-glycolide (PLGA), poly(phosphazine), poly (phosphate ester), polycaprolactones, polyanhydrides, ethylene vinyl acetate, polyorthoesters, polyethers, and poly (beta amino esters). Other polymers include polyamides, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), polyvinyl acetate, poly vinyl chloride, polystyrene, polyvinylpyrrolidone, poly(butyric acid), poly(valeric acid), and poly(lactide-cocoaprolactone). Peptides, polypeptides, proteins such as collagen or albumin, polysaccharides such as sucrose, chitosan, dextran, alginate, hyaluronic acid (or derivatives or combinations of any of these), dendrimers (e.g., PAMAM dendrimers), dextrins, cyclodextrins may be used in various embodiments. Methods for preparation of such formulations will be apparent to those skilled in the art. Liposomes or other lipid-containing particles can be used in some embodiments. Exemplary polymers include cellulose derivatives such as, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxymethylcellulose, carboxylethyl cellulose, cellulose triacetate, cellulose sulphate sodium salt, polycarbamates or polyureas, Chemical derivatives of the aforementioned polymers, e.g., substitutions, additions of chemical groups, for example, alkyl, alkylene, hydroxylations, oxidations, and other modifications routinely made by those skilled in the art can be used.

A pacifier or dosage form of the invention may be packaged in a container marked to indicate that its contents include an allergen and/or to depict one or more allergen(s) or allergen source(s) and/or may feature a brand name, logo, etc.

A person of ordinary skill in the art will understand that preventative therapies may be allergen specific and allergens may be selected to target particular clinically relevant concerns. In some embodiments, allergens may be selected based on a history of allergy in one or more of the infant's biological relatives (e.g., biological parent, grandparent, sibling). For example, if an infant has a family history of allergy to particular allergen(s), the infant may be at increased risk of developing allergy to those particular allergen(s) (or immunologically cross-reactive allergens). Genetic testing could be used to identify infants predisposed to develop allergy. In some embodiments of the invention, a composition contains one or more allergen(s) of relevance to a particular geographic area. For example, the allergen(s) can be allergen(s) of plants (e.g., pollen allergens) that grow commonly in such area, and/or allergen(s) of fungi, insects, mites, etc., that are commonly found in such area. In some embodiments, a composition contains one or more allergen (s) that are significant causes of allergy in a geographical area. In some embodiments, an allergen is a significant cause of allergy if it is among the 5 most commonly diagnosed allergy-causing agents in a particular category (e.g., airborne, ingested, skin contact) in a geographical area. Diagnosis may be based on, e.g., skin prick testing or other methods accepted in the art. A geographical area can be a continent, e.g., North America, South America, Europe, Asia, Africa, Australia; one or more countr(ies), regions, or jurisdictions (e.g., US, Canada, Mexico, Argentina, Brazil, Chile, Venezuela, European Union, Belgium, Denmark, France, Germany, Italy, Netherlands, Norway, Poland, Spain, Sweden, Switzerland, United Kingdom, Turkey, Russia, Eurasia, Israel, Japan, China, Korea, India, Pakistan, Philippines, Singapore, Vietnam, Thailand, Indonesia, Egypt, South Africa, ARIPO member state(s), Australia, etc.) or portion(s) thereof (e.g., one or more states or provinces). A geographical region can be defined based at least in part on climate or other natural features. In some embodiments a geographical area is at least 10,000 $km^2$ in area.

As known in the art, many allergens are immunologically cross-reactive with other allergens, e.g., allergens that share at least some similar or identical epitopes (e.g., IgE antibodies that bind to a first allergen will also bind to allergens that share at least some similar or identical epitopes). Thus an individual who is allergic to an allergen from a first species will often be allergic to other allergens, e.g., allergens from related species. In some embodiments, a first allergen may be used to prevent or reduce risk of developing allergy to a second allergen. The first and second allergens may be derived from different sources. For example, in the case of allergens of plant, animal, or fungal origin, the first and second allergens may be derived from different species within a genus, or different genera within a subfamily or family, or different subfamilies within a family. For example, in some embodiments, the invention contemplates use of a pollen allergen from one or more grasses or trees of a first subfamily to prevent or reduce risk of developing allergy to pollen of one or more grasses or trees of a second subfamily. In some embodiments, the invention contemplates use of pollen allergen from trees of the subfamily Cupressoideae (e.g., junipers) to prevent or reduce risk of developing allergy to pollens of the subfamily Taxodioidea (e.g., Japanese cedar), or vice versa. For example, Japanese cedar pollen allergens can be immunologically cross reactive with allergens of *Cupressus sempervirens, Juniperus ashei, Cupressus arizonica, Cupressus macrocarpa, Juniperus virginiana, Juniperus communis, Thuya orientalis*, and/or *Chamaecyparis obtusa*.

A person of ordinary skill in the art will understand that specific attributes of the pacifier may be altered or adapted without departing from the spirit nor limiting the scope of the instant invention as defined by the claims. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. For example, any allergen or ingredient, etc., can be explicitly excluded. Applicants reserve the right to proviso out of the claims any specific allergen, allergen category, ingredient, ingredient category, or combination thereof, whether or not such allergen, ingredient, category, or combination thereof, is recited herein. To the extent, if any, that a pacifier, or a composition for use in a pacifier that is known or described in the prior art may include an allergen, the instant invention may be distinguished from such prior art pacifier or composition in, for example, any one or more of the following ways: (i) the pacifier or composition of the invention comprises one or more allergen(s) not present in the prior art pacifier or composition; (ii) the pacifier or composition of the invention comprises a different amount of allergen, or a different form of the allergen, than present in the pacifier or composition; (iii) the product or composition of the invention explicitly excludes the allergen(s) present in the prior art pacifier or composition; (iv) the composition of the invention comprises at least one ingredient not present in the prior art composition or present in a different amount and/or omits at least one ingredient present in the prior art composition.

The invention claimed is:

1. A method for reducing a risk of developing a hyperallergenic immune system disorder in a human at increased risk of developing a hyperallergenic immune system, the method comprising: exposing the oral mucosa of a human infant to at least daily sustained contact with a composition comprising: a polymeric delivery vehicle formulated as a matrix, wherein the polymer is selected from polypeptide, polysaccharide, synthetic polymer, and mixtures thereof; and one or more allergens mixed with a protein stabilizer, wherein the human infant is between the ages of birth and about three months when daily sustained contact is initiated, and daily sustained contact continues thereafter for at least about three months, wherein "exposing" is achieved by providing the infant with a pacifier comprising a synthetic nipple comprising pores, said pacifier being adapted for containment of the composition and controlled dispersion of the composition over the oral mucosa upon suckling activity by the infant, wherein dispersion is controlled by selection of nipple pore size, composition viscosity, and binding character of the vehicle matrix.

2. The method according to claim 1 wherein the one or more allergens are selected from the group consisting of: food, pollen, dust mite, mold, animal dander, and combinations thereof.

3. The method according to claim 2, wherein the pollen is a ragweed pollen and the selected allergens consist of ragweed pollen and dust mite.

4. The method according to claim 1 wherein the pacifier comprises a base member and a nipple member comprising the porous synthetic nipple.

5. The method according to claim 4, wherein the pacifier is provided to the infant for suckling on a schedule that permits daily sustained contact for at least one hour.

6. The method according to claim 1 wherein the infant has an atopic constitution and the one or more allergens are selected to restore a Th1/Th2 balance.

7. The method according to claim 1 wherein the hyperallergenic immune system disorder is an IgE-mediated disorder comprising allergic rhinitis and/or allergic asthma.

8. A method for restoring a T1/T2 balance in a human infant by promoting induction of a Th1-biased immune response during a developmentally critical period, the method comprising: exposing the oral mucosa of the human infant to at least daily sustained contact with one or more allergens for a period of at least about three months, wherein the daily sustained contact is initiated when the infant is between the ages of birth and about three months and is achieved by providing the infant with a pacifier adapted for containment of a composition comprising: a polymeric delivery vehicle formulated as a matrix, wherein the polymer is selected from polypeptide, polysaccharide, synthetic polymer, and mixtures thereof; and the one or more allergens mixed with a protein stabilizer and further adapted for controlled dispersion of the composition over the oral mucosa upon suckling activity by the infant, wherein dispersion is controlled by selection of nipple pore size, composition viscosity, and binding character of the vehicle matrix.

9. The method according to claim 8, wherein the daily sustained contact is initiated when the infant is between the ages of birth and about two weeks.

10. The method according to claim 8, wherein the daily sustained contact is initiated within 48 hours of birth and continues until the infant is about three months of age.

11. The method of claim 1, wherein the allergen comprises a *Cryptomeria japonica* pollen allergen or an allergen that is immunologically cross-reactive therewith.

12. The method of claim 1, wherein the allergen comprises a grass pollen allergen or an allergen that is immunologically cross-reactive therewith.

13. The method of claim 1, wherein the allergen comprises a pollen allergen, optionally a *Cryptomeria japonica* pollen allergen or grass pollen allergen or an allergen that is immunologically cross-reactive therewith.

14. The method of claim 1, wherein the allergen consists of a food allergen or an allergen that is immunologically cross-reactive therewith.

15. The method according to claim 14, wherein the food allergen is selected from a peanut, tree nut, egg, milk, shellfish, fish, wheat, or soy allergen, and combinations thereof.

16. The method according to claim 14, wherein the food allergen is provided as an extract from fresh food.

17. The method according to claim 1, wherein the protein stabilizer comprises glycerin.

* * * * *